United States Patent [19]

Henzel

[11] 4,031,884

[45] June 28, 1977

[54] APPARATUS FOR CORRELATING THE RESPIRATORY AND CARDIAC CYCLES

[75] Inventor: Daniel Georges Christian Henzel, Noisy le Grand, France

[73] Assignee: Institut National de la Sante et de la Recherche Medicale, Paris, France

[22] Filed: June 2, 1975

[21] Appl. No.: 583,184

[30] Foreign Application Priority Data

June 7, 1974 France .............................. 74.19669

[52] U.S. Cl. ..................... 128/2.05 R; 128/DIG. 29
[51] Int. Cl.² ....................... A61B 5/02; A61B 5/08
[58] Field of Search ......... 128/2.05 R, 2 R, 2.06 R, 128/2.1 R, 2.1 Z, 2.08, DIG. 29

[56] References Cited

UNITED STATES PATENTS

| | | | |
|---|---|---|---|
| 3,513,832 | 5/1970 | Klemm et al. ................. | 128/2.05 R |
| 3,572,317 | 3/1971 | Wade ............................. | 128/2.05 R |
| 3,618,592 | 11/1971 | Stewart .......................... | 128/2.06 R |
| 3,871,361 | 3/1975 | Kamen ........................... | 128/2.05 R |

*Primary Examiner*—Robert W. Michell
*Assistant Examiner*—Lee S. Cohen
*Attorney, Agent, or Firm*—Oblon, Fisher, Spivak, McClelland & Maier

[57] ABSTRACT

An apparatus for correlating the respiratory and cardiac cycles includes a circuit for defining a chosen period in the progress of the respiratory cycle as the end of a regulatable delay beginning when the ascending front of the inspiratorial pressure reaches a regulatable level as well as a circuit for defining a chosen period in the progress of the cardiac cycle as the end of a regulatable delay beginning when the differential $dV/dt$ of the blood pressure reaches a regulatable level. An operator such as a terminal relay is activated upon the coincidence of these two periods in time after a regulatable delay and during a regulatable period.

9 Claims, 5 Drawing Figures

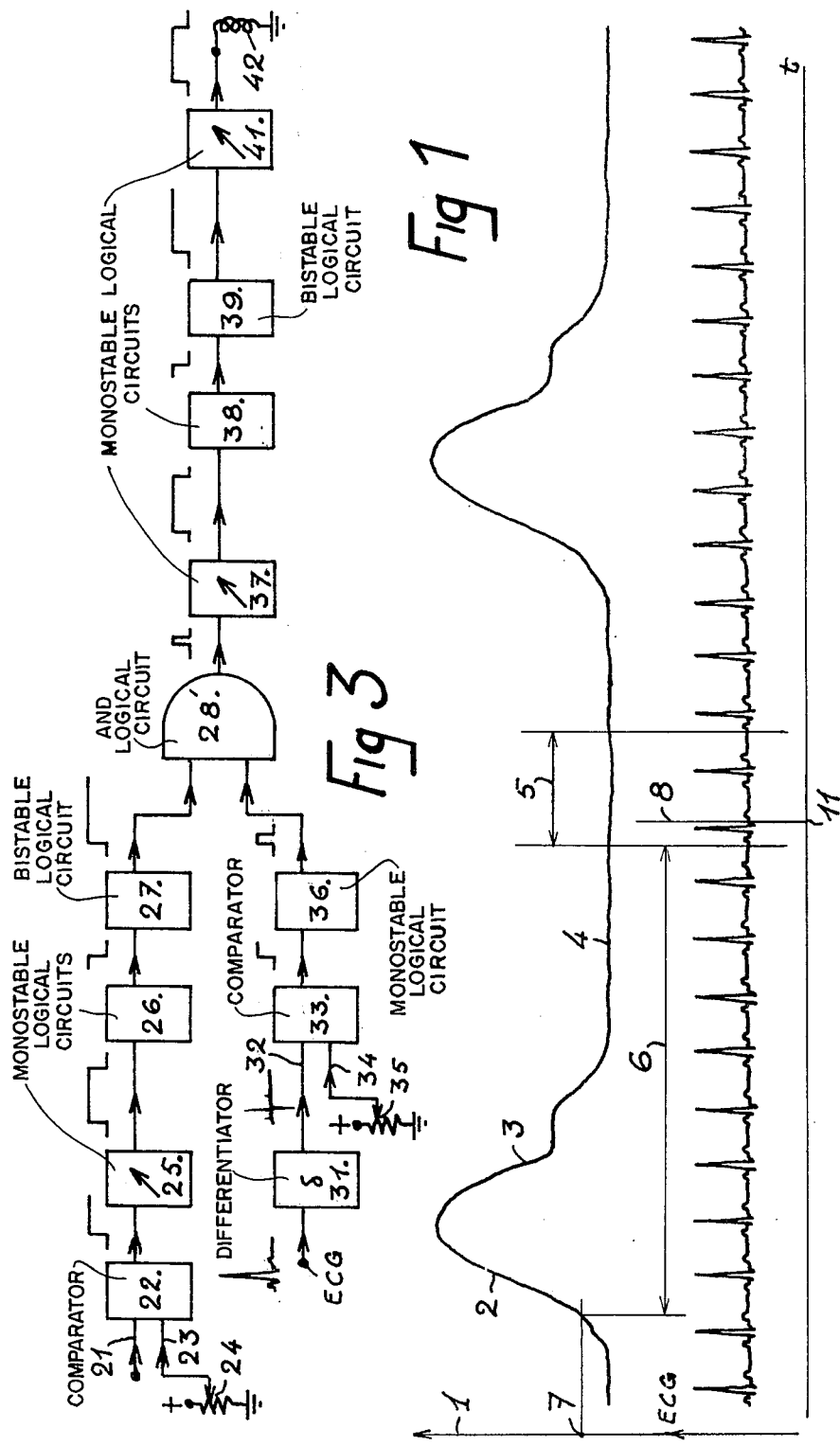

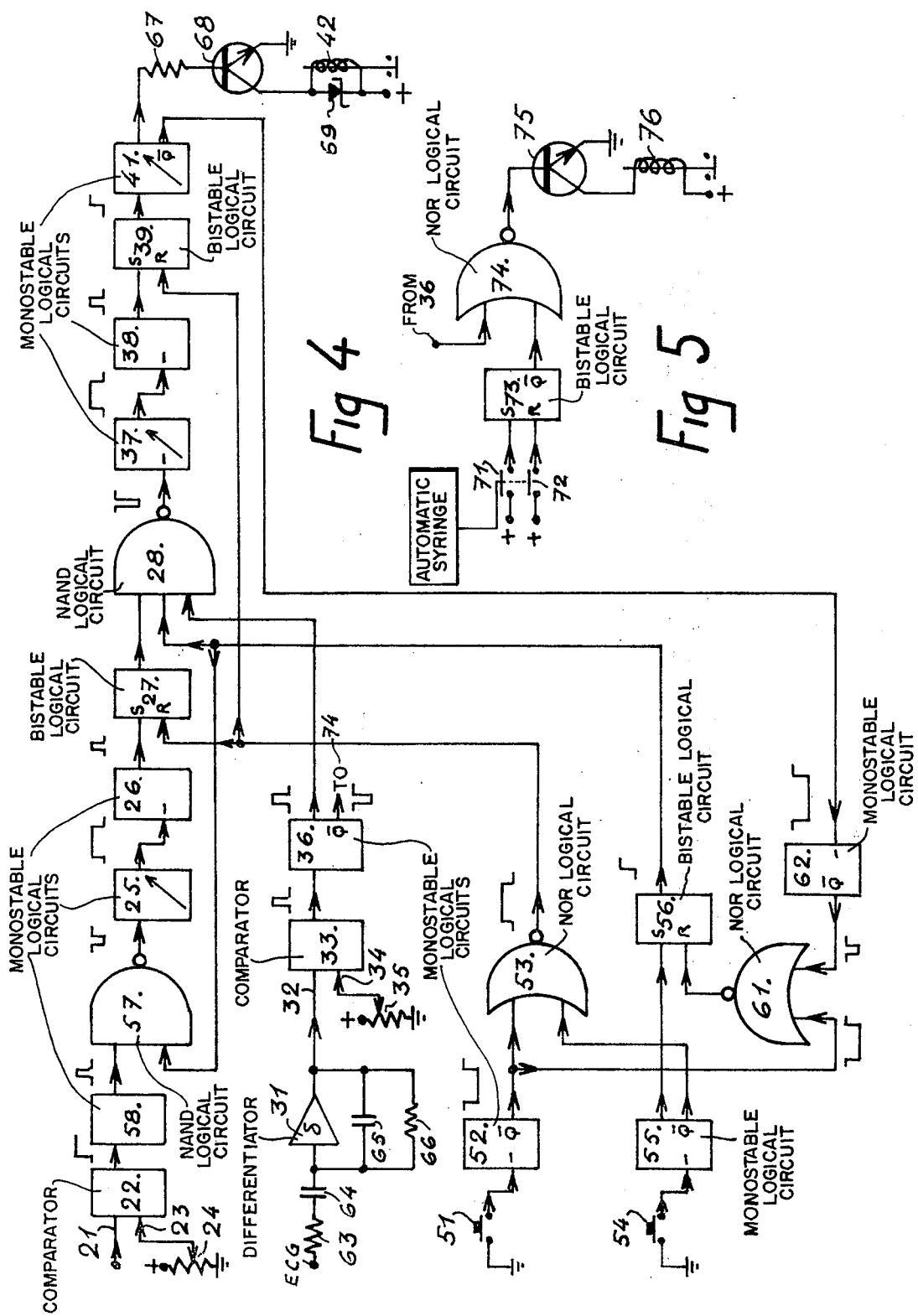

APPARATUS FOR CORRELATING THE RESPIRATORY AND CARDIAC CYCLES

BACKGROUND OF THE INVENTION

The invention concerns apparatus for correlating the respiratory and cardiac cycles, i.e., apparatus capable of recognizing the moment at which the patient (or the animal) is simultaneously at a precise and chosen period in the progress of his respiratory cycle and at a precise and chosen period in the progress of his cardiac cycle. At this moment, the apparatus yields a signal which can control any selected apparatus, and particularly, but not exclusively, an automatic injector, controlled by the electrocardiagram, for measuring the cardiac output.

The correlation between the respiratory and cardiac cycles could be recognized by a human operator, but, the apparatus of this invention, besides offering the advantages inherent in an automatic mechanism, is equipped with improvements that are only possible under automation, and certain ones of these improvements make it possible for the apparatus to function in pathological cases that are beyond the capabilities of a human operator.

The use of the apparatus of the invention is not, of course, limited to the measurement of cardiac output. On the contrary, it extends to mechanisms used in radiology, and, in particular, pulmonary radiography of infants or patients in coma, and to angiocardiography.

In pulmonary radiography, it is necessary that certain radiological negatives of the pulmonary apparatus be taken at the moment of expiration or at the moment of inspiration. It is an object of the apparatus of this invention to fill this need.

Angiocardiography is the radiological method which reveals the cardiac cavities or the vessels and the blood which circulates there by means of injection of a substance which is opaque to X-rays. The patient undergoing the examination has a catheter placed in his vein, which makes it possible to inject the opaque substance where desired. Thereupon, a series of negatives is made as needed.

The results of these examinations depend upon the respiratory or cardiac cycles. It is thus important that the taking of these negatives be automatized in relation to these two functions, which makes it possible to obtain negatives relating to various moments in these cycles. The apparatus according to this invention was, again, designed in order to fill this need.

SUMMARY OF THE INVENTION

The foregoing and other objects are obtained with the present invention. According to the apparatus of the invention, the precise and chosen period in the progress of the respiratory cycle is defined as the end of a regulatable delay (for example, up to ten seconds) beginning when the ascending front of the inspiratorial pressure reaches a regulatable level. The precise and chosen period in the progress of the cardiac cycle is defined as the end of a regulatable delay (for example, up to one millisecond) beginning when the differential $dV/dt$ of the blood pressure reaches a regulatable level. When these two points coincide, an operator such as a terminal relay is set in motion after a regulatable delay (for instance up to one second) and during a regulatable period (for instance up to one second).

The definition for the respiratory cycle is both unique and precise since it is based on the ascending front of the inspiratorial pressure and the ascending front is always regular while the descending front is sometimes irregular (step-like, or even with dips). The definition for the cardiac cycle is also both unique and precise since, in the blood pressure wave, the ventricular systole has an ascending front near its beginning which always (when measured with the classic electrodes) has a gradient (thus a differential $dV/dt$) much greater than that of the rest of the electrocardiagram, even in pathological cases.

It is clear that the blood pressure wave can be picked up by any known method, and especially, though not exclusively, by an ECG electrocardiogram.

In the case of the application to pulmonary radiography discussed above, the signal of respiratory pressure may, for instance, be supplied by a pneumotachograph, the outlet of which operates the two inlets of the apparatus of the invention. The delay authorizing the taking of the negatives is recorded in the inspiratorial pressure canal P, and a zero delay is recorded in the blood pressure canal ECG.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 1 is a graph of the inspiratorial pressure of the electrocardiogram in function of time;

FIG. 2 is a detail in enlarged scale of the electrocardiogram according to FIG. 1;

FIG. 3 is a block diagram illustrating the principle of the invention;

FIG. 4 is a block diagram of a preferred model of the invention for use in measuring cardiac output;

FIG. 5 is a block diagram of an improvement that functions in cooperation with the block diagram according to FIG. 4.

DETAILED DESCRIPTION OF A PREFERRED EMBODIMENT

Referring now to the drawings, wherein like reference numerals designate identical or corresponding parts throughout the several views, and more particularly to FIG. 1 thereof, FIG. 1 shows a cyclical diagram in function of time, of the inspiratorial pressure 1 of the patient (or the animal) placed under the respirator. This inspiratorial pressure 1 presents a hump, the ascending front 2 of which is always regular, while its decending front 3 is sometimes of irregular form (with a horizontal portion as shown or even with a dip or rise). This hump is followed by a horizontal portion 4, on which the user chooses a period 5. This period 5, for the apparatus of the invention, is defined by the end of a regulatable delay 6 beginning when the ascending front 2 reaches a regulatable level 7. The ECG electrocardiogram (shown at the bottom of FIG. 1), is of a period 10 to 20 times shorter than the period of the respiratory cycle, and its classic form PQRST is more easily readable in the enlarged detail of FIG. 2. The user chooses a period 8 on the horizontal portion between S and T. For the apparatus of the invention, this period 8 is defined by the end of a regulatable delay 9 beginning when the differential $dV/dt$ of the electrocardiogram reaches a regulatable level such that only the ascending front QR of the ventricular systole attains this level. With reference again to FIG. 1, when the periods 5 and 8 defined according to the invention coincide in time, i.e., at the first moment 11 where period 8 appears during period 5, the initial point of control of the selected operator is reached, for instance, a terminal relay is reached.

With reference to FIG. 3, which is a block diagram illustrating the principle of the invention, the inspiratorial pressure is applied to an input 21 of a comparator 22, the other input of which, 23, receives a voltage regulated by a potentiometer 24. The comparator 22 activates a monostable logical circuit 25, the duration of the unstable state of which can be regulated up to 10 seconds (this is the regulatable delay 6). A monostable logical circuit 26, the duration of the unstable state of which is 1 millisecond, responds to the rear front portion of the output signal of the monostable logical circuit 25 causing a bistable logical circuit 27, which activates an input of a logical circuit and 28', to fluctuate. On the other hand, the ECG electrocardiograph is attached to the input of a differentiator circuit 31, which transmits the differential $dV/dt$ to an input 32 of a comparator 33, the other input 34 of which receives a voltage regulated by a potentiometer 35. The comparator 33 activates a monostable logical circuit 36, the duration of the unstable state of which is 1 millisecond, which activates, during this period, the other input of the circuit and 28', which, at the moment 11, sends a signal to a monostable logical circuit 37, the duration of the unstable state of which can be regulated up to 1 second (this is the delay 9). A monostable logical circuit 38, the duration of the unstable state of which is 1 millisecond, responds to the rear front portion of the output signal of the monostable logical circuit 37 causing a bistable logical circuit 39, which activates a monostable logical circuit 41 with an unstable state regulatable up to 1 second, to fluctuate. During its regulatable time, the monostable logical circuit 41 feeds an operator, which in this case is a terminal relay 42. FIG. 3 is, in principle, a block diagram, in the sense that on the one hand, the different blocks are not described in detail, because each of them can be constructed according to whatever means are available to the technician, and, on the other hand, the means of starting and stopping are not described, nor are the positive order of the initial position of the bistable circuits before starting and other improvements which the invention incorporates and which will be described in the following.

Reference will now be made to FIG. 4 which is a block diagram of a preferred model of the invention for use in measuring cardiac output. In FIG. 4 the elements described in relation to FIG. 3 are present. FIG. 4 also contains the positive order of the initial position of the bistable circuits before starting, and the elements for starting and stopping the mechanism. For the positioning, a spring push-button 51 activates the input of the monostable logical circuit 52, the duration of the unstable state of which is 20 seconds, and which activates during this period a logical circuit nor 53, which in turn activates the reset inputs R of the bistable logical circuits 27 and 39 (previously described), which are thus placed in positive position. For the starting operation, spring push-button 54 activates the negative input of a monostable logical circuit 55, with an unstable state of 100 microseconds duration, which activates, during this period, the set input S of a bistable logical circuit 56. Bistable logical circuit 56 then feeds the input of a logical circuit Nand 57, the other input of which is activated by a monostable circuit 58, with an unstable state of 1 millisecond duration, located at the output of the comparator 22 (previously described with relation to FIG. 3). The output of the logical circuit Nand 57 activates the input of the monostable logical circuit 25 (previously described in relation to FIG. 3). Thus, the way for the respiratory pressure signal between comparator 22 and monostable logical circuit 25 is only established if bistable logical circuit 56 is in set position. Simultaneously, bistable logical circuit 56 activates a third input of the logical circuit NAND 28 so that the same condition for the signal way beyond logical circuit NAND 28 is present. Moreover, the monostable circuit 52, the positioning circuit, activates a logical circuit NOR 61, which activates the reset input R of the bistable logical circuit 56. Thus, bistable logical circuit 56 is also positioned positively by the positioning push-button 51. Finally, the reversed output Q of the monostable logical circuit 41 activates the negative input of a monostable logical circuit 62, the duration of the unstable state of which is much less than 1 millisecond, and which activates another input of the logical circuit NOR 61, thus resetting the bistable logical circuit 56 at a resting position. Incidentally, the differentiater 31 is serially connected with a series filter RC 63–64, and in parallel with a parallel filter RC 65–66, both with a time constant of 0.1 seconds, e.g., $R = 100 \, K\Omega$ and $C = 1 \, \mu f$, the object of which is to dilate the vertical QRS of the ECG while leveling out the P and T waves. The direct output of the monostable logical circuit 41 indirectly feeds the terminal relay 42, through a resistor 67 and a transistor 68, with a diode 69 to protect against overvoltages.

The function of the apparatus shown in FIG. 4 will now be described. As soon as the voltage is turned on, the positioning button 51 is pressued activating the monostable logical circuit 52. The logical circuit NOR 53 transmits an impulse to bistable circuits 27, 39 and 56, which are in a resetting position, while the circuits NAND 57 and 28 are blocked. Preliminary adjustments are then made; adjustment of the threshold 7 of the inspiratorial pressure by means of the potentiometer 24 of the comparator 22, adjustment of the differentiated threshold of the ECG by means of the potentiometer 35 of the comparator 33, adjustment of the delay 6 of the inspiratorial pressure by means of the regulatable monostable circuit 25, adjustment of the delay 9 of the ECG by means of the regulatable monostable circuit 37, and adjustment of the duration of function by means of the regulatable monostable circuit 41. To set the mechanism in function, the start button 54 is depressed, the monostable circuit 55 moves the bistable circuit 56 into a set position, which permits the unblocking of the circuit NAND 57 and, through circuit NOR 53, confirms the preliminary positioning of the bistable circuits 27 and 39 in a resting position. The pressure signal is received by the comparator 22, the monostable circuit 58 unblocks the circuit NAND 57, the monostable circuit 25 delays the impulse that activates the monostable 26 placing the bistable 27 in working position which permits the unblocking of the circuit NAND 28. On the ECG side, the monostable circuit 36 releases an impulse in synchronization with the beginning of the QRS which unblocks the circuit NAND 28. The monostable circuit 37 delays the impulse that activates the monostable circuit 38 placing the bistable circuit 39 in a set position thus setting the monostable circuit 41. The terminal relay 42 is fed during the period selected. At the same time, the monostable circuit 41 feeds the monostable circuit 62 which resets the bistable circuit 56 at its resetting position by means of circuit NOR 61, and, thereupon, there is a general return to the zero position (previously described).

For measuring cardiac output, the terminal relay 42, by means of its connections, controls an automatic rapid syringe, of which there are several models commercially available. On the other hand, when recording the progress of the concentration of the indicator injected through the syringe, the moment and the duration of the injection, as well as marking of the cardiac cycle, e.g., of the QRS wave of the electrocardiogram, should be recorded. A description follows of how the invention fulfills these requirements.

With reference to FIG. 5, when the automatic syringe begins its injection course, it closes a connection 71, and when it has completed its course, it closes a connection 72. The connection 71 places a bistable circuit 73 in a set position S, and the contact 72 returns it to resetting position R. During the injection, the reversed output Q of the bistable circuit 73 activates an input of a logical circuit NOR 74. The other input of this circuit 74 is activated by the reversed output Q of the monostable circuit 36 (of FIG. 4) at each ascending side QR of the ECG. Thus, during the injection and at each side NOR of the ECG, the circuit NOR 74 feeds a transistor 75 and a relay 76, the contact of which control a marking instrument of the recorder, for example, by short circuiting the recording input of the inspiratorial pressure.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by letters patent of the United States is:

1. An apparatus for correlating respiratory and cardiac cycles comprising:
    means for defining a chosen period in the progress of the respiratory cycle as the end of a regulatable delay beginning when the ascending front of the inspiratorial pressure reaches a regulatable level,
    means for defining a chosen period in the progress of the cardiac cycle as the end of a regulatable delay beginning when the differential $dV/dt$ of the blood pressure reaches a regulatable level,
    means for activating an operator upon the coincidence of these two periods in time after a regulatable delay and during a regulatable period.

2. An apparatus according to claim 1 in which the cardiac cycle period defining means includes means for connection to an electrocardiograph.

3. An apparatus according to claim 1 wherein:
    the respiratory cycle period defining means includes a first comparator with a regulatable threshold for the inspirational pressure, a first monostable logical circuit connected to the first comparator and having an unstable state whose duration can be regulated for up to 10 seconds, a second monostable logical circuit with an unstable state of one millisecond connected to the first monostable logical circuit and responsive to the rear front portion of the signal generated by the first monostable logical circuit, and a first bistable logical circuit connected to the second monostable logical circuit,
    the cardiac cycle period defining means includes a differentiator circuit for the blood pressure, a second comparator connected to the differentiator circuit and having a threshold activated by the differentiator circuit, and a third monostable logical circuit with an unstable state of one millisecond connected to the second comparator, and
    the operator activating means includes a first logical NAND circuit activated by and connected to the first bistable logical circuit and the third monostable logical circuit, a fourth monostable logical circuit having an unstable state the duration of which can be regulated for up to one second connected to the first logical NAND circuit a fifth monostable logical circuit with an unstable state of one millisecond connected to the fourth monostable logical circuit and responsive to the rear front portion of the signal generated by the fourth monostable logical circuit, a second bistable logical circuit connected to the fifth monostable logical circuit, and a sixth monostable logical circuit having an unstable state duration which can be regulated for up to one second connected to the second bistable logical circuit to feed the operator.

4. An apparatus according to claim 3 wherein the first and second bistable logical circuits have reset inputs R and further comprising first push-button means for the initial positioning of the first and second bistable logical circuits, a seventh monostable logical circuit with an unstable state and having a negative input connected to and activated by the push-button means, and logical NOR circuit means connected to the seventh monostable logical circuit for activating the reset inputs R of the bistable logical circuits.

5. An apparatus according to claim 4 further comprising second push-button means, an eighth monostable logical circuit with an unstable state of 100 microseconds and having a negative input connected to and activated by the second push-button means, a third bistable logical circuit having a set input S and a reset input R, the set input S connected to and activated by the eighth monostable logical circuit, the output of the third bistable logical circuit connected to an input of the first NAND logical circuit, and wherein the respiratory cycle defining means includes a ninth monostable logical circuit with an unstable state of one millisecond serially connected to the first comparator, and a second logical NAND circuit activated by and connected to the third bistable logical circuit and the ninth monostable logical circuit.

6. An apparatus according to claim 5 further comprising a second NOR logical circuit means for activating the reset input R of the third bistable logical circuit and having a plurality of inputs, one input being connected to and activated by the seventh monostable logical circuit.

7. An apparatus according to claim 6 further comprising a tenth monostable logical circuit with an unstable state of much less than one millisecond and a negative input connected to and activated by the reversed output of the sixth monostable logical circuit, the output of the tenth monostable logical circuit being connected to another input of the second logical NOR circuit means.

8. An apparatus according to claim 3 wherein the differentiator circuit is arranged in series with a series filter RC and in parallel with a parallel filter RC and both filters have a time constant of 0.1 seconds.

9. An apparatus according to claim 3 further comprising an automatic syringe equipped with a starting contact to start an injection for the measurement of cardiac output and a stopping contact to end the injection for the measurement of cardiac output, a fourth bistable logical circuit having a set input S connected to and activated by the starting contact and a reset input R connected to and activated by the stopping contact, a third logical NOR circuit means having two inputs, one input of the third logical NOR circuit means connected to and activated by the reversed output of the fourth bistable logical circuit and the other input of the third logical NOR circuit means connected to and activated by the reversed output of the third monostable logical circuit, and relay means connected to the third logical NOR circuit means for controlling the marker of an external recording element.

* * * * *